United States Patent [19]
Stiffey

[11] Patent Number: 5,130,251
[45] Date of Patent: Jul. 14, 1992

[54] STRESS-RESISTANT BIOLUMINESCENT DINOFLAGELLATES

[75] Inventor: Arthur V. Stiffey, Slidell, La.

[73] Assignee: The United States of America as represented by the Secretary of the Navy, Washington, D.C.

[21] Appl. No.: 754,145

[22] Filed: Sep. 3, 1991

Related U.S. Application Data

[63] Continuation-in-part of Ser. No. 534,082, Jun. 6, 1990, abandoned.

[51] Int. Cl.⁵ .............................................. C12N 1/12
[52] U.S. Cl. .................................... 435/257; 435/946
[58] Field of Search ................................ 435/257, 946

Primary Examiner—Elizabeth C. Weimar
Assistant Examiner—Suzanne Ziska
Attorney, Agent, or Firm—Thomas E. McDonald; Alfons F. Kwitnieski

[57] ABSTRACT

A tough mutant strain of the bioluminescent marine dinoflagellate pyrocystis lunula which produces almost three times more light than its predecessor Pyrocystis lunula strain, which can withstand much more centrifugal force than its predecessor, and which grows faster than its predecessor in a defined medium under laboratory conditions, doubling about every four days, and requiring only monthly transfers.

4 Claims, No Drawings

STRESS-RESISTANT BIOLUMINESCENT DINOFLAGELLATES

This is a continuation-in-part of U.S. patent application Ser. No. 07/534,082, filed Jun. 6, 1990, now abandoned of Arthur V. Stiffey for "Stress-Resistant Bioluminescent Dinoflagellates".

BACKGROUND OF THE INVENTION

1. Field of the Invention

The invention relates to a robust, stress-resistant, mutant strain of the bioluminescent marine dinoflagellate *Pyrocystis lunula*.

2. Description of the Related Art

Luminescent bacteria have been used for many years as the assay organism in various commercial toxicity tests, as described in Chapter 4, "Bioluminescence Assays" by Anthony A. Bulich, pp. 57-74 in G. Bitton and B. J. Dutka (eds.) TOXICITY TESTING USING MICRO ORGANISMS, Vol. I, CRC Press, Boca Raton, Fla.

NRL Memorandum Report 5738 by Hannan, Stiffey and Jarvis dated Mar. 17, 1986 and entitled Bioluminescence as the Basis for the Detection of Trichothecenes describes the use of the marine dinoflagellate *Pyrocystis lunula* for detecting a diminution of light output which could indicate the presence of certain trichothecenes, popularly known as "yellow rain" compounds. Of the nine trichothecenes tested, five had no effect on the dinoflagellates, but four caused a dimunition of light output of the *Pyrocystis lunula*.

Until the development of the stress-resistant organism described and claimed herein, the bioluminescent dinoflagellate *Pyrocystis lunula* was not used as the assay organism in a commercial bioassay, perhaps because *Pyrocystis lunula* is a relatively fragile organism, easily killed by rough handling or moderate centrifugal forces.

STATEMENT OF DEPOSIT

On Feb. 13, 1990, a mutant *Pyrocystis lunula* cell line was deposited in the American Types Culture Collection, 12301 Parklawn Drive, Rockville, Md. 20852 and assigned ATCC Deposit No. 40752. On May 7, 1991, this mutant *Pyrocystis lunula* cell line was replaced with another mutant *Pyrocystis lunula* cell line corresponding to the present invention.

SUMMARY OF THE INVENTION

The invention provides *Pyrocystis lunula* cells which generate almost three times more light than predecessor *Pyrocystis lunula* cells under the same conditions and which are capable of withstanding a centrifugal force of 2600 times the pull of gravity for 10 minutes with only about a ten percent reduction in light output.

DETAILED DESCRIPTION OF THE INVENTION

The progenitors of the mutant *Pyrocystis lunula* described and claimed herein were taken from the South Atlantic Ocean in 1972 by Dr. Elijah Swift from the University of Rhode Island. To maintain the organisms in their original nutritional state, Dr. Swift grew them in f/2 medium including seawater from the Sargasso Sea. F/2 medium is well-known to the art, and is the same as the medium f described in Table II, page 231, Volume 8 (1962) of the Canadian Journal of Microbiology in a paper by Gaillard and Ryther entitled STUDIES OF MARINE PLANKTONIC DIATOMS, except f/2 medium is diluted by sea water to 2 liters whereas medium f is diluted by sea water to 1 liter.

In 1974, Dr. Richard Lynch of the Naval Research Laboratory, Washington, D. C., obtained a transfer of these *Pyrocystis lunula* cells and grew them in an f/2 medium supplemented by seawater collected 15 miles off the Maryland coast. Dr. Lynch's culture of *Pyrocystis lunula* was given to Dr. Arthur V. Stiffey in 1981 when he first started to work at the Naval Research Laboratory in the field of bioluminescence, and Dr. Stiffey has experimented with and been responsible for this line of *Pyrocystis lunula* since that time.

When Dr. Lynch's culture of *Pyrocystis lunula* was given to Dr. Stiffey, it was hopelessly contaminated with other algae of a nonbioluminescent type, so the *Pyrocystis lunula* cells were reisolated and placed in a modified f/2 medium. This medium was chemically defined and adapted to the development of a microbiological assay that would detect chemicals suppressing bioluminescence. The medium was f/2 with the omission of silica, the addition of carbonate ion, and the addition of Lyman-Fleming artificial sea water which is prepared with C. P. salts and distilled water from the formula of Lyman and Fleming, "Composition of Sea Water", J. Mar. Res. 3, 134, 1940, tabulated in Table VII for synthetic sea water of chlorinity 19.0%. The pH was initially adjusted to 9.0, but after approximately three years, the pH was changed to 7.6 to permit the assaying of a larger variety of chemicals. The pH since then has been maintained at 7.6.

Since 1982, Dr. Stiffey's culture of *Pyrocystis lunula* has been used as a microbiological assay organism to detect a variety of chemical compounds that depress bioluminescence, as, for example, those described in the above-referenced NRL Memorandum Report 5738. This *Pyrocystis lunula* assay organism contains many cysts which emit light when the organism is subjected to a shear stress, such as in stirring. It has a slow rate of growth (doubling time is approximately four days) and transfers need only be done monthly. These organisms require no special handling and benefit from very static conditions. Stock cultures contain approximately 2000 cell/ml.

Over the years, Dr. Stiffey gradually became aware that his *Pyrocystis lunula* were tougher and easier to manipulate than what was considered normal for *Pyrocystis lunula*. For example, he inadvertently transported a culture of these cells in the trunk of his automobile from Washington to New York on a hot sunny midsummer day, and the *Pyrocystis lunula* cells were unaffected by the jostling and high temperature. Also, these *Pyrocystis lunula* cells were unharmed after centrifugation treatments usually quite destructive to algal cells.

To determine if Dr. Stiffey's *Pyrocystis lunula* strain had mutated and how its characteristics had changed from that of Dr. Swift's *Pyrocystis lunula* strain, the progenitor of Stiffey's strain, samples of Dr. Swift's *Pyrocystis lunula* strain were sent by air express from the University of Rhode Island to Dr. Stiffey at Stennis Space Center, Ms. Upon receipt, the cells of Dr. Swift's strain were microscopically examined with few cells being found. The cultures were placed in an incubator at Dr. Swift's recommended temperature and light cycle. The cells were not bioluminescent after one week in the incubator undisturbed; they were dead. Thereafter, Dr. Swift sent three tubes of another culture, only one of which survived the trip and produced light when agitated. Dr. Swift's *Pyrocystis lunula* culture has been maintained in Dr. Stiffey's modified f/2 medium described above, although it apparently grows much slower than Stiffey's *Pyrocystis lunula* strain.

Various experiments have been performed to determine the differences or sameness of selected characteristics of Swift's *Pyrocystis lunula* strain and Stiffey's *Pyrocystis lunula* strain, as described below.

Shape and Size

The lunate cells of both *Pyrocystis lunula* strains were similar in shape and size. The distances between the horns of intact cells, selected at random, were found not to differ at less than 1% level of confidence between the two strains. These distances were measured under a microscope with a calibrated ruled eyepiece.

Light output

In this experiment, the light output of a first set of 10 aliquots of Stiffey's *Pyrocystis lunula* having 100 cells/ml was compared to the light output of a second set of 10 aliquots of Swift's *Pyrocystis lunula* having 100 cells/ml and also compared to the light output of a third set of 10 aliquots of Swift's *Pyrocystis lunula* having 200 cells/ml. Both cultures were in the stationary growth phase when tested. The number of cells tested was 300 per aliquot for the first and second sets and 600 per aliquot for the third set, for a comparison of 3000 cells of Stiffey's culture versus 3000 cells and 6000 cells of Swift's culture.

Both *Pyrocystis lunula* cultures were incubated at 20° C. plus or minus 1° C. in Stiffey's modified f/2 medium described above. Illumination was provided by cool white fluorescent lamps, shaded to obtain a light intensity of 17 micro einsteins/cm$^2$. Illumination was on a cycle of 12 hours light and 12 hours dark. The cells of both *Pyrocystis lunula* cultures were counted with the aid of a Sedgewick Rafter chamber and their concentration adjusted to 100 cells per ml. for the first and second sets of aliquots, and adjusted to 200 cells per ml. for the third set of aliquots.

The first set of ten 3 ml aliquots of Stiffey's *Pyrocystis lunula* culture at 100 cells/ml, the second set of ten 3 ml aliquots of Swift's *Pyrocystis lunula* at 100 cells/ml, and the third set of ten 3 ml aliquots of Swift's *Pyrocystis lunula* culture at 200 cells/ml were dispensed respectively into thirty glass vials, 22 mm. diameter ×55 mm. length. These vials containing the test cultures were placed in a carousal and kept motionless in the dark for several hours prior to testing.

To be certain that each *Pyrocystis lunula* test culture emitted the maximum quantity of light, it was necessary that the culture be stirred vigorously. Stirring was accomplished with an acrylic rod equipped on one end with a thin strip of acrylic plastic. The other end of the rod was fitted into the chuck of a variable speed electric motor drive set at about 1000 rpm. During the assay of each test vial, the rod was inserted approximately ⅔ of the way into the test culture, and stirring was continued for about two minutes to make sure that the light producing ability of the *Pyrocystis lunula* cells was exhausted.

The bioluminescence of each test culture was measured with a solid state photometer described in U.S. Pat. No. 4,689,305 to Stiffey et al, incorporated herein by reference. A multi-range stripchart recorder with a chart speed of 5 cm/minute was connected to the photometer which was adjusted such that the recorder registered the cumulative light fluxes as a function of time.

The light outputs (in arbitrary units) of these thirty *Pyrocystis lunula* test cultures, are given in the following tabulation:

| Sample No. | Stiffey's Strain 100 cells/ml | Swift's Strain 100 cells/ml | Swift's Strain 200 cells/ml |
|---|---|---|---|
| 1 | 95 | 35 | 68 |
| 2 | 93 | 33 | 75 |
| 3 | 93 | 37 | 71 |
| 4 | 99 | 32 | 72 |
| 5 | 97 | 39 | 78 |
| 6 | 95 | 37 | 79 |
| 7 | 97 | 33 | 71 |
| 8 | 92 | 35 | 69 |
| 9 | 95 | 32 | 70 |
| 10 | 99 | 39 | 69 |
| Average light output | 95.5 | 35.2 | 72.2 |
| Standard Deviation | 2.33 | 2.56 | 3.65 |
| Coefficient of Variation | 2.4% | 7.2% | 5.0% |

Thus, the average light output of Stiffey's *Pyrocystis lunula* strain (95.5) is 271 per cent greater than the average light output of Swift's *Pyrocystis lunula* strain (35.2).

Toughness

The reaction of Stiffey's *Pyrocystis lunula* culture to centrifugation was compared with the reaction of Swift's *Pyrocystis lunula* culture to the same centrifugation to determine their relative toughness, i.e., the ability to withstand stress.

Aliquots of Stiffey's *Pyrocystis lunula* culture and Swift's *Pyrocystis lunula* culture were counted in a Sedgewick Rafter counting chamber and both cultures were adjusted to have 100 organisms per milliliter.

Each of twenty centrifuge tubes were filled with 10 ml of Stiffey's *Pyrocystis lunula* culture adjusted to 100 cells/ml. Similarly, each of twenty other centrifuge tubes were filled with 10 ml of Swift's *Pyrocystis lunula* culture adjusted to 100 cells/m. Four tubes of Stiffey's *Pyrocystis lunula* culture and four tubes of Swift's *Pyrocystis lunula* culture were reserved as controls and were not centrifuged. Four tubes of Stiffey's *Pyrocystis lunula* culture and four tubes of Swift's *Pyrocystis lunula* culture were centrifuged for ten minutes at 1000 rpm in a centrifuge having a centrifuge holder radius of 15. 5 cm., which corresponds to a centrifugal force exerted on the cultures of 150 G's, according to a nomograph for converting centrifuge rpm to centrifugal force, given in METHOD OF IMMUNOLOGY (Third Edition) by Harvey, Cremer, and Sussdorf, published in 1977 by W. A. Benjamin, Inc., Reading, Mass. Four tubes of Stiffey's *Pyrocystis lunula* culture and four tubes of Swift's *Pyrocystis lunula* culture were centrifuged for ten minutes at 2000 rpm, which corresponds to a centrifugal force of 600 G's. Four tubes of Stiffey's *Pyrocystis lunula* culture and four tubes of Swift's *Pyrocystis lunula* culture were centrifuged for ten minutes at 4000 rpm, which corresponds to a centrifugal force of 2100 G's. The remaining four tubes of Stiffey's *Pyrocystis lunula* culture and four tubes of Swift's *Pyrocystis lunula* culture were centrifuged for ten minutes at 5000 rpm, which corresponds to a centrifugal force of 2600 G's.

Since the light producing ability of all the centrifuged *Pyrocystis lunula* cells was exhausted during the centrifuging process, all twenty of the tubes of *Pyrocystis lunula* cultures were maintained motionless in the dark for several hours to allow the centrifuged *Pyrocystis lunula* cells to replenish their light producing capabilities. Thereafter, the bioluminescence of each of the twenty *Pyrocystis lunula* cultures was measured in the same way as described above, by vigorously stirring the culture until the light producing ability of the *Pyrocystis lunula* cells is exhausted while measuring the total light emission of these *Pyrocystis lunula* cells with the photometer described in U.S. Pat. No. 4,689,305, which generates an output voltage proportional to the total light emission. The results of this experiment are shown in the following tabulation of the photometer output voltage (total light emission) for all twenty *Pyrocystis lunula* cultures.

|  | Centrifual Force | | | | |
| --- | --- | --- | --- | --- | --- |
|  | 1 G | 150 G | 600 G | 2100 G | 2600 G |
|  | Stiffey's Strain | | | | |
|  | .89 | .88 | .87 | .86 | .83 |
|  | .92 | .87 | .86 | .84 | .82 |
|  | .91 | .90 | .83 | .83 | .80 |
|  | .88 | .89 | .81 | .84 | .79 |
| Average Output | .90 | .885 | .8425 | .8425 | .81 |
| Standard Deviation | 1.58 | 1.11 | 2.38 | 1.08 | 1.58 |
| Coefficient of Variation | 1.7% | 1.26% | 2.7% | 1.28% | 1.9% |
|  | Swift's Strain | | | | |
|  | .75 | .70 | .57 | .40 | .32 |
|  | .77 | .68 | .58 | .43 | .31 |
|  | .76 | .65 | .50 | .41 | .34 |
|  | .68 | .67 | .51 | .39 | .29 |
| Average Output | .74 | .675 | .54 | .4075 | .315 |
| Standard Deviation | 3.53 | 1.8 | 3.5 | 1.47 | 1.80 |
| Coefficient of Variation | 4.7% | 1.5% | 6.5% | 3.6% | 5.7% |

This experiment indicates that Stiffey's *Pyrocystis lunula* can withstand centrifugal forces up to 2600 G's for 10 minutes with only a 10% reduction in light producing capability, whereas Swift's progenitor *Pyrocystis lunula* cannot withstand a centrifugal force of only 600 G's for 10 minutes without a much larger reduction (27%) in light producing capability.

In this centrifugal force test, the photometer output voltage was arbitrarily adjusted to a value when Stiffey's *Pyrocystis lunula* were tested than was different from the value when Swift's *Pyrocystis lunula* were tested. Thus, the relative light outputs of the twenty tubes of Stiffey's *Pyrocystis lunula* are relative only to each other. Similarly, the relative light outputs of the twenty tubes of Swift's *Pyrocystis lunula* are relative only to each other.

However, the ratio of the average light output of the four control tubes of Swift's *Pyrocystis lunula* to the average light output of the four control tubes of Stiffey's *Pyrocystis lunula* should be essentially the same as the ratio (35.2/95/5) determined in the light output test described above. Thus, the average photometer output voltages (average light outputs) of this test can be expressed as a percentage of the average output of the four control tubes of Stiffey's *Pyrocystis lunula* (.90 v.), as shown below.

| | RELATIVE LIGHT OUTPUT | | | | |
| --- | --- | --- | --- | --- | --- |
| CENTRIFUGAL FORCE | 1 G | 150 G | 600 G | 2100 G | 2600 G |
| Stiffey's Strain | 100.0 | 98.7 | 93.6 | 93.6 | 90.0 |
| Swift's Strain | 36.9 | 33.6 | 26.9 | 20.3 | 15.7 |

Under rough handling conditions, the light output advantage of Stiffey's *Pyrocystis lunula* over Swift's strain increases.

What is claimed and desired to be secured by letters patent of the United States is:

1. A biologically pure culture of the mutant *Pyrocystis lunula* cell line ATCC 40752.

2. A mutant *Pyrocystis lunula* strain, as described in claim 1, which has a light output at least 200 per cent of the light output of predecessor *Pyrocystis lunula* Swift's strain under identical test conditions.

3. A biologically pure culture of mutant *Pyrocystis lunula* strain ATCC 40752, (1) which can withstand for ten minutes a centrifugal force 2100 times the force exerted on a cell by gravity when the cell is at rest, wherein the light output is at least 90 percent of the light output at 1 G, and (2) which has a light output at least 200 per cent of the light output of predecessor *Pyrocystis lunula* Swift's strain under identical test conditions.

4. A *Pyrocystis lunula* strain, as described in claim 1, which can withstand for ten minutes a centrifugal force 2100 times the force exerted on the cell by gravity when the cell is at rest, wherein the light output is at least 90 percent of the light output of 1 G.

* * * * *